United States Patent
Bergstrom et al.

(12)

(10) Patent No.: US 6,653,395 B1
(45) Date of Patent: Nov. 25, 2003

(54) ORTHOESTER-BASED POLYMER AS WELL AS PREPARATION AND USE THEREOF

(75) Inventors: Karin Bergstrom, Kungalv (SE); Per-Erik Hellberg, Svenshogen (SE)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 09/202,906

(22) PCT Filed: Jun. 5, 1997

(86) PCT No.: PCT/SE97/00987

§ 371 (c)(1),
(2), (4) Date: Dec. 23, 1998

(87) PCT Pub. No.: WO98/00452

PCT Pub. Date: Jan. 8, 1998

(30) Foreign Application Priority Data

Jul. 2, 1996 (SE) ................................................ 9602617

(51) Int. Cl.$^7$ ........................ C07C 43/32; C08G 65/32; C11D 1/72
(52) U.S. Cl. ........................ 524/599; 528/271; 528/425; 568/595
(58) Field of Search ........................ 524/599; 528/271, 528/425; 568/595

(56) References Cited

U.S. PATENT DOCUMENTS 2,867,667 A    1/1959   Dermer et al.
3,903,006 A    9/1975   Elliott et al. .................. 252/79

FOREIGN PATENT DOCUMENTS

EP    0 054 366    6/1982
EP    0 564 402    10/1993

OTHER PUBLICATIONS

Nikitin "the chemistry of Cellulose and Wood", pp. 62–71 (1966).*

Hiemenz in *Polymer Chemistry*, p 34–43. Marcel Dekker, 1984.*

Fried in *Polymer Science and Technology*, "1.3 Molecular Weight", p. 16–18. Prentice Hall, 1995.*

Mandelkern in *An Introduction to Macromolecules*, p. 19–27. Springer–Verlag, 1983.*

*International Search Report*, dated Oct. 16, 1997.

* cited by examiner

*Primary Examiner*—Jeffrey Mullis
(74) *Attorney, Agent, or Firm*—Ralph J. Mancini

(57) ABSTRACT

The present invention relates to new orthoester-based block polymers having a good antifoaming effect in liquid aqueous systems. The compounds are easily biologically degradable and, compared with traditional block polymers, have a comparatively high cloud point, which makes them readily compatible with other compounds and facilitates the formulation of homogeneous compositions. The new polymers are characterized in that they contain a block of at least 4 alkyleneoxy groups having 3 and/or 4 carbon atoms.

8 Claims, No Drawings

ORTHOESTER-BASED POLYMER AS WELL AS PREPARATION AND USE THEREOF

The present invention relates to new orthoester-based block polymers having a good antifoaming effect in liquid aqueous systems. The compounds are easily biologically degradable and, compared with traditional block polymers, have a comparatively high cloud point, which makes them readily compatible with other compounds and facilitates the formulation of homogeneous compositions.

Block polymers containing hydrophobic blocks based on alkylene oxides, such as propylene oxide and/or butylene oxide, and hydrophilic blocks based on ethylene oxide, are a well-known group of compounds having a good antifoaming effect in liquid aqueous systems. However, they are difficult to degrade biologically and have relatively low cloud points. Other types of compounds with antifoaming effect are silicone compounds, which in many applications cannot be used owing to the absorption of the silicone compounds to solid materials. Other examples are nonionic surface-active ethylene oxide adducts, where the ethyleneoxy chain has been terminally blocked with one or more alkyleneoxy alkyl groups having 3–4 carbon atoms or an alkyl group having 1–4 carbon atoms. These compounds are in themselves low-foaming and thus not very efficient as antifoaming agents. Besides, they are comparatively difficult to degrade biologically.

EP 564 402 discloses the preparation of surface-active low-foaming orthoesters by using as reactant an addition product of ethylene oxide to a hydroxyl-containing aliphatic compound having 8–26 carbon atoms. The resulting products have higher foaming than traditional block polymers between ethylene oxide and propylene oxide and are not suitable for use as antifoaming agent. Moreover, in degradation ethylene oxide adducts are formed, which are foaming and have high surface activity, which are inconvenient properties from the viewpoint of application as well as environment. Alkylene-glycol-containing orthoesters are also disclosed in U.S. Pat. No. 2,867,667 and U.S. Pat. No. 3,903,006. The latter patent specification states that owing to, among other things, a suitable viscosity at −40° C., it can be used in hydraulic fluids.

The object of the present invention is to find compounds which have a good antifoaming effect at least on the same level as known block polymers and which are easily biologically degradable and, in degradation, form intermediate products having low foaming, toxicity and surface activity. Moreover, they should have good wettability and high cloud points.

It has now been found that orthoester-based polymers have a good antifoaming effect in liquid aqueous systems, while they are easily biologically degradable compared with conventional block polymers. The intermediate products formed in degradation have low foaming, toxicity and surface activity. Besides, the hydrophobic-hydrophilic balance of the compounds can easily be changed such that the wettability and cloud point in water are adapted to the properties desired for different applications. The new polymers are of the general formula

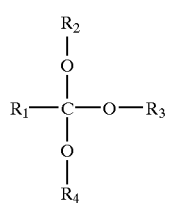

(I)

wherein $R_1$ is hydrogen or a hydrocarbon group having 1–4 carbon atoms; $R_2$ is a group $(A)_nY$, where each A is an ethyleneoxy group or a higher alkyleneoxy group having 3–4 carbon atoms, n is a number 0–100, and each Y is hydrogen or an alkyl group having 1–4 carbon atoms, provided that when Y is hydrogen, n is a number from 1 to 100, $R_3$ and $R_4$ are groups of the formula $(A)_nY$, where A, n and Y have the above meaning, or a di- or polycondensate of the polymers via free hydroxyl groups in $R_2$, $R_3$ or $R_4$, the total sum of all n being 8–2,500, preferably 8–200, and that at least one of the groups $R_2$, $R_3$ and $R_4$ contains at least one block of at least 4, usually 4–50, preferably 6–20 alkyleneoxy groups having 3 and/or 4 carbon atoms. Preferred polymers are those where the total number of ethyleneoxy groups in the polymers is 0–80%, preferably 5–60%, based on the total number of alkyleneoxy groups and higher alkyleneoxy groups and a molecular weight of 600–100,000, preferably 800–10,000.

By varying the number and types of alkyleneoxy groups in the groups $R_2$, $R_3$ and $R_4$ and their positioning in the groups, and by terminally blocking the groups with alkyl groups, the properties, such as solubility, cloud point, floatability, wettability, melting point and antifoaming effect, of the orthoester-based block polymers can be varied and combined in various ways according to their different fields of application. In contrast to traditional block polymers, which usually have an antifoaming effect which is strongly temperature-dependent, the inventive block polymers, which usually are present in the form of a product mixture, have low sensitivity to variations in temperature and can therefore be used in wide temperature ranges. Examples of fields where the block polymers can be used as antifoaming agent are in milk substitute compositions, in chemical processes, such as emulsion polymerisation, in metal working fluids and other industrial functional fluids, in dishwasher formulations and in industrial cleaning, in cosmetics, lubricants and liquid plant protection compositions etc.

Examples of suitable polymers according to the invention are those of the general formula

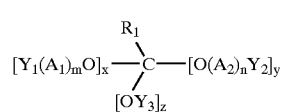

(II)

wherein $R_1$ has the above meaning, each $A_1$ is an alkyleneoxy group having 3–4 carbon atoms, m is from 4 to 40, each $Y_1$ is hydrogen or an alkyl group having 1–4 carbon atoms, each $A_2$ is an alkyleneoxy group having 2–4 carbon atoms, $Y_2$ is hydrogen or a hydrocarbon group having 1–4 carbon atoms, n is a number from 2 to 40, $Y_3$ is an alkyl group having 1–4 carbon atoms, x is 1, 2 or 3, preferably 1 or 2, y is 0, 1, 2 or 3, preferably 0 or 1, and z is 0, 1 or 2, preferably 0 or 1, the sum of x, y and z being 3. Preferably $Y_1$ and $Y_2$ are an alkyl group having 1–4 carbon atoms. When preparing the compounds according to the invention, a mixture of compounds according to the invention is usually obtained owing to the process of preparation. A common average value of x is 1.0–2.1, y is 0.1–1.8 and z is 0.2–1.8. In formula II, $Y_1$, $Y_2$ and $Y_3$ are preferably a methylene or ethylene group. The groups $A_1$ are preferably propyleneoxy groups, while the groups $A_2$, usually to at least 10%, preferably to at least 50%, consist of ethyleneoxy groups. If $A_2$ consists of both ethyleneoxy and higher alkyleneoxy groups, these can be added in blocks or at random, or a combination thereof.

The compounds according to the invention can be prepared by reacting, in one or more steps, an orthoester of the general formula

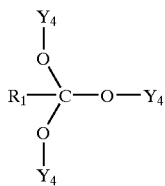

wherein $R_1$ has the above meaning and $Y_4$ designates a hydrocarbon group having 1 or 4 carbon atoms, with reactants of the formulae $HOR_2$, $HOR_3$ and $HOR_4$, wherein $R_2$, $R_3$ and $R_4$ have the above meaning, suitably in the presence of an acid catalyst, such as methanesulphonic acid. As the reaction proceeds, the released hydroxyl-containing compound $Y_4OH$ is removed, where $Y_4$ has the above meaning, at an increasing temperature, which in the final phase of the reaction suitably is 140–220° C. The final phase of the reaction is usually also carried out under vacuum. Conveniently, the reaction is carried out in several steps. For example, the reactants containing secondary hydroxyl groups can be reacted before reactants containing primary hydroxyl groups. If dimerisation or a higher degree of merisation is desired, diols having in the first place primary hydroxyl groups, but also diols having secondary hydroxyl groups are suitably selected, and triols or hydroxyl compounds having a large number of hydroxyl groups, which optionally are secondary, may be used.

The present invention is further illustrated by the following Examples.

EXAMPLE 1

One mole of polypropylene glycol having an average molecular weight of 400 was reacted with 0.66 mole triethyl orthoformate in the presence of 0.01% by weight methanesulphonic acid. Of the alkyl substituents of the orthoformate, 2 of 3 were desired to be replaced by bonds to the polypropylene glycol. Ethanol, which was released during the reaction, was distilled off continuously from the reaction mixture. The temperature in the reaction mixture was increased successively as the reaction proceeded so as to be between 150° C. and 200° C. in the final stage of the reaction. The final phase of the reaction was carried out at reduced pressure so as to facilitate the removal of ethanol. After completion of the reaction, 59.2 g ethanol had been distilled off, which corresponds to 97.3% of the desired theoretical value. Subsequently, 0.33 mole monomethyl-blocked polyethylene glycol having an average molecular weight of 350 was added to the triethyl orthoformate-polypropylene glycol adduct as resulting above, while removing ethanol at reduced pressure. The product mixture was then analysed with $^1$H-NMR, $^{13}$C-NMR, GPC and hydroxyl number determination, which indicated that the resulting, partly polymerised orthoformate had an average substitution of about 1.9, bound to a polypropylene glycol chain, an average substitution of about 0.5 bound to methyletherpolyethylene glycol groups, an average substitution of about 0.6 ethyl groups. The average molecular weight was about 1550.

EXAMPLE 2

One mole of polypropylene glycol having an average molecular weight of 400 was reacted with 1.4 mole triethyl orthoformate in the presence of 0.01% by weight methanesulphonic acid. The reaction was carried out in the same manner as in Example 1 during continuous distilling off of ethanol. After the reaction was determined to be completed, the distilled-off quantity of ethanol amounted to 90.5% of the theoretical value. Then 0.17 mole monomethyl-block polyethylene glycol having an average molecular weight of 350 was added and reacted with the reaction mixture containing triethyl orthoformate-polypropylene glycol adducts while removing ethanol at reduced pressure. The resulting product was analysed in the same manner as in Example 1, and it was indicated that the polymerised orthoformate had a polypropylene glycol substitution of, on average, about 1.3 and a methyletherpolyethylene glycol substitution of about 0.1, and an ethyl substitution of about 1.6. The average molecular weight was about 1,900.

EXAMPLE 3

One mole of monoethyl-blocked polyethylene glycol having an average molecular weight of about 220 and 2 mole monoethyl-blocked polypropylene glycol having an average. molecular weight of 450 was reacted simultaneously with 1 mole triethyl orthoformate in the presence of 0.01% by weight methanesulphonic acid. The reaction was carried out as in Examples 1 and 2 above. The product mixture was analysed with $^1$HNMR, $^{13}$C-NMR, GPC and hydroxyl number determination. The analyses indicated that the product did not contain any unreacted triethyl orthoformate, and that the resulting orthoformate compounds had on average an ethyl substitution of about 0.2, an ethyletherpolyethylene glycol substitution of about 0.9, an ethyletherpolypropylene glycol substitution of about 1.9 and an average molecular weight of about 1,050. The five greatest, in terms of weight, compounds in the reaction mixture were composed as follows.

TABLE 1

| | Compound | | | | |
|---|---|---|---|---|---|
| | 1 | 2 | 3 | 4 | 5 |
| Substituent | | Number of substituents | | | |
| —$C_2H_5$ | — | — | — | 1 | 1 |
| —$(OC_2H_4)_nOC_2H_5$ average molecular weight 220 | 1 | — | 2 | 0 | 1 |
| —$(OC_3H_6)_mOC_2H_5$ average molecular weight 450 | 2 | 3 | 1 | 2 | 1 |
| % by weight of the total amount of product mixture | 20 | 12.5 | 12.5 | 12.5 | 10 |

EXAMPLE 4

The heights of foam, that were produced by different block polymers in a 500 ml measuring glass, which was rotated about its horizontal axis at a speed of 40 rpm during 3 min, were measured immediately after completion of the rotation and after 1 min. Moreover, the average life of a bubble was determined according to Bikerman at a flow rate of between 38 and 59 ml nitrogen gas/s and at a concentration of 20 ppm of the block polymer. The tested block polymers and the results obtained are apparent from the Table below.

TABLE 2

| EO/PO-block polymer | Berol 370 | Berol 374 | Pluronic PE 8100 | Ex 1 | Ex 2 |
|---|---|---|---|---|---|
| Average molecular weight | 1400 | 2200 | 2550 | 1550 | 1900 |
| Cloud point, °C., | | | | | |
| 15% butanol diglycol | 42 | 33 | 37 | 60 | 57 |
| Height of foam, mm | | | | | |
| 0 min | 42 | 31 | 19 | 10 | 0 |
| 1 min | 0 | 0 | 0 | 0 | 0 |
| Bikerman, s | 4 | 3 | — | 1 | — |

As appears from the results, the block polymers according to the invention had, at comparable molecular weights, a lower foaming combined with higher cloud points than the comparison products.

EXAMPLE 5

The defoaming of block polymers on foaming protein-containing aqueous solutions was measured at room temperature. The experiment was carried out by blowing nitrogen gas through the solution at a flow rate of 38 ml/s during 150 s, during which the height of foam was read as a function of time. The composition of the solution was 0.050% bovine albumin and 0.500% sodium hydroxide. 0.025% by weight of antifoaming agent was added to the solution according to the Table below. The following results were obtained.

TABLE 3

| Antifoaming agent | Height of foam, cm | | | | | | | |
|---|---|---|---|---|---|---|---|---|
| | 10 s | 20 s | 30 s | 40 s | 60 s | 80 s | 100 s | 150 s |
| — | 11.5 | 21.0 | 32 | 40 | >40 | >40 | >40 | >40 |
| Berol 374 | 8.3 | 14.2 | 19.2 | 23.5 | 29.5 | 34.7 | 37.3 | >40 |
| Pluronic PE 8100 | 4.0 | 6.5 | 8.0 | 8.0 | 9.2 | 10.2 | 11.2 | 13.2 |
| Ex. 1 | 0 | 0 | 0 | 0 | 0 | 0 | 0 | 0 |

As appears from the results, the block polymer according to the invention had the best antifoaming effect in the test.

EXAMPLE 6

Defoaming of different block polymers on an alkylglycoside-containing formulation was carried out by measuring the height of foam in a double-walled column, provided with a finely pored glass filter and nozzle for injecting nitrogen gas in the bottom. The solution was poured into the column and nitrogen gas was blown through the solution at a fixed flow rate during 30 s, whereupon the nitrogen gas was shut off and the height of foam was read as a function of time. The experiments were carried out at 20° C. and 40° C. Alkylglycosides are known for their good foaming effect. The concentrations of used antifoaming agents were 0.0025% by weight or 0.0050% by weight. The alkylglycoside formulation was composed as follows:

| Compound | % by weight |
|---|---|
| $C_{10}$ alkylglycoside | 0.025 |
| $C_6$ alkylglycoside | 0.004 |
| Tetrapotassium polyphosphate | 0.03 |
| Sodium metasilicate | 0.02 |

The following results were obtained.

TABLE 4

| Antifoaming agent | Conc. % by weight | 30 s | 60 s | 90 s | 120 s |
|---|---|---|---|---|---|
| | | Defoaming, mm at 20° C. | | | |
| — | — | 801 | 220 | 45 | 45 |
| Berol 374 | 0.0025 | 88 | 477 | 113 | 45 |
| | 0.0050 | 817 | 272 | 11 | 11 |
| Ex. 2 | 0.0025 | 261 | 11 | 0 | 0 |
| | 0.0050 | 165 | 0 | 0 | 0 |
| EP 564 402, Ex.5 | 0.0025 | 953 | 511 | 193 | 125 |
| | 0.0050 | 1010 | 568 | 204 | 40 |
| | | Defoaming, mm at 40° C. | | | |
| — | | 987 | 363 | 102 | 74 |
| Berol 374 | 0.0025 | 623 | 0 | 0 | 0 |
| Ex. 2 | 0.0025 | 499 | 22 | 17 | 17 |
| EP 564 402, Ex.5 | 0.0025 | 1056 | 567 | 227 | 136 |

As appears from the results, the antifoaming agent according to the invention had a good antifoaming effect at both 20° C. and 40° C. and was superior to the comparison products.

EXAMPLE 7

A plant protection formulation of the following composition was formulated.

| Compound | % by weight |
|---|---|
| Glyphosate | 20 |
| Tertiary fatty amine ethoxylate | 3.5 |
| Antifoaming agent | 0.4 |
| Water (ion-exchanged) | balance |

2 ml of the formulation was diluted to 200 ml with ion-exchanged water. These 200 ml were then transferred to a measuring glass holding 500 ml, which was rotated at a speed of 40 rpm. The height of foam was then read at fixed intervals. The following results were obtained.

TABLE 5

| Antifoaming agent | Height of foam, mm/Time, sek | | | | |
|---|---|---|---|---|---|
| | 0 s | 30 s | 60 s | 90 s | 120 s |
| — | 159 | 128 | 47 | 15 | 10 |
| Berol 370 | 71 | 66 | 48 | 35 | 25 |
| Example 2 | 36 | 25 | 18 | 15 | 12 |
| Example 3 | 65 | 44 | 16 | 12 | 9 |

As appears from the results, the inventive antifoaming agent was superior to the comparison antifoaming agent.

EXAMPLE 8

The biodegradability of the block polymer containing orthoesters according to the invention was compared with the biodegradability according to a traditional block polymer (Berol 374). The following results were obtained.

TABLE 6

| Antifoaming agent | Biodegradability, % | |
|---|---|---|
|  | 14 days | 28 days |
| Berol 374 | 0 | 3 |
| Example 1 | 6 | 69* |
| Example 2 | 21 | 62* |

*easily biodegradable

As appears from the results, the orthoesters according to the invention are easily biodegradable, whereas the traditional block polymer represented by Berol 374 is difficult to degrade.

What is claimed is:

1. An orthoester-based polymer having the general formula

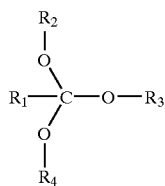

(I)

wherein $R_1$ is hydrogen or a hydrocarbon group having 1–4 carbon atoms; $R_2$ is a group $(A)_nY$, where each A is an ethyleneoxy group or a higher alkyleneoxy group having 3–4 carbon atoms, and each Y is hydrogen or an alkyl group having 1–4 carbon atoms, provided that when Y is hydrogen, n is a number from 1 to 100, $R_3$ and $R_4$ are groups of the formula $(A)_nY$, where A, n and Y have the above meaning, or a di- or polycondensate of the polymer via free hydroxyl groups in $R_2$, $R_3$ or $R_4$, the total sum of all n being 8–2,500, and that at least one of the groups $R_2$, $R_3$ and $R_4$ contains at least one block of at least 4 alkyleneoxy groups having 3 and/or 4 carbon atoms.

2. The polymer of claim 1 wherein the sum of all n is 10–200, and that at least one of the groups $R_2$, $R_3$ and $R_4$ contains at least one block of 6–20 alkyleneoxy groups having 3–4 carbon atoms.

3. The polymer of claim 1 having the general formula

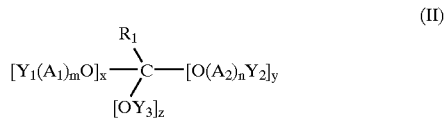

(II)

wherein $R_1$ in hydrogen or a hydrocarbon group having 1–4 carbon atoms, each $A_1$ is an alkyleneoxy group having 3–4 carbon atoms, m is from 4 to 40, each $Y_1$ is hydrogen or an alkyl group having 1–4 carbon atoms, $A_2$ is an alkyleneoxy group having 2–4 carbon atoms, $Y_2$ is hydrogen or a hydrocarbon group having 1–4 carbon atoms, n is a number from 2 to 40, $Y_3$ is an alkyl group having 1–4 carbon atoms, x is 1, 2 or 3, y is 0, 1, 2 or 3, and z is 0, 1 or 2, the x, y and z being 3.

4. The polymer of claim 3 wherein $Y_1$ and $Y_2$ are an alkyl group having 1–4 carbon atoms.

5. A polymer mixture which comprises at least one of the polymers of claim 3 wherein the average value of x is 1.0–2.1, the average value of y is 0.1–1.8 and the average value of z is 0.2–1.8.

6. The polymer mixture of claim 1 wherein $R_1$ is hydrogen.

7. A method of preparing the polymer of claim 1 which comprises reacting, in one or more steps, an orthoester of the general formula

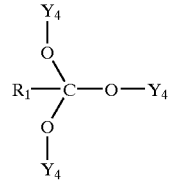

wherein $R_1$ is hydrogen or a hydrocarbon group having 1–4 carbon atoms and $Y_4$ designates a hydrocarbon group having 1 or 4 carbon atoms with reactants of the formulae $HOR_2$, $HOR_3$ and $HOR_4$, wherein $R_2$, $R_3$ and $R_4$ have the meanings stated in claim 1, by removing released hydroxyl-containing compounds of formula $Y_4OH$, where $Y_4$ is a hydrocarbon group having 1 or 4 carbon atoms.

8. An antifoaming agent in liquid aqueous systems which comprises the polymer of claim 1.

* * * * *